United States Patent [19]

Gates

[11] Patent Number: 5,401,710
[45] Date of Patent: Mar. 28, 1995

[54] HERBICIDES

[75] Inventor: Peter S. Gates, Cambridge, England

[73] Assignee: Schering Agrochemicals Limited, Cambridge, United Kingdom

[21] Appl. No.: 87,691

[22] PCT Filed: Jan. 6, 1992

[86] PCT No.: PCT/GB92/00018
§ 371 Date: Jul. 9, 1993
§ 102(e) Date: Jul. 9, 1993

[87] PCT Pub. No.: WO92/11763
PCT Pub. Date: Jul. 23, 1992

[30] Foreign Application Priority Data

Jan. 9, 1991 [GB] United Kingdom ............ 91100406

[51] Int. Cl.⁶ ............... C07D 239/47; C07D 239/42; C07D 239/48; A01N 43/54
[52] U.S. Cl. ..................... 504/239; 544/320; 544/323; 544/332; 504/242; 504/243
[58] Field of Search .............. 504/242, 243, 239; 544/332, 320, 323

[56] References Cited

FOREIGN PATENT DOCUMENTS 0155872 9/1985 European Pat. Off. .
0372326 6/1990 European Pat. Off. .

OTHER PUBLICATIONS

Gilmore, Chemical Abstracts, vol. 93, entry 239328v (1980).
Lespagnol, Chemical Abstracts, vol. 64, entry 6649g (1966).

*Primary Examiner*—John M. Ford
*Attorney, Agent, or Firm*—Ostrolenk, Faber, Gerb & Soffen

[57] ABSTRACT

Herbicidal compositions which comprise one or more compounds of the formula:

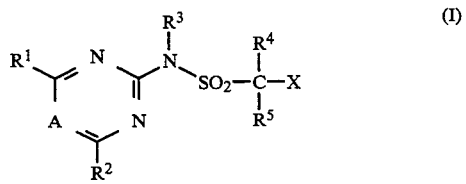

or salts thereof, where:

A is —CH= or —N=;
$R^1$ is alkyl, alkoxy, halo or —$NR^7R^8$;
$R^2$ is alkyl or alkoxy;
$R^3$ is hydrogen, alkenyl or alkynyl, or substituted or unsubstituted alkyl, alkanoyl or alkoxycarbonyl;
$R^4$ is hydrogen or substituted or unsubstituted alkyl;
$R^5$ is halo or substituted or unsubstituted alkyl or aryl; and
X is —$CO_2R^6$, —$CONR^7R^8$ or —CN;
in which $R^6$, $R^7$ and $R^8$, which may be the same or different, each represent hydrogen, substituted or unsubstituted alkyl, or one of $R^7$ and $R^8$ represents substituted amino;
in association with a suitable carrier and/or surface active agent, together with the compounds of formula I per se where $R^5$ represents isopropyl, and/or X represents methoxycarbonyl, and salts thereof.

20 Claims, No Drawings

HERBICIDES

FIELD OF THE INVENTION

This invention concerns sulfonamidopyrimidines and sulfonamidotriazines having herbicidal activity, processes for their preparation and herbicidal compositions containing them.

PRIOR ART

In European Patent Specification No 155872, there are described certain arylsulfamoyl acetic acid derivatives useful for reducing the lignin content of crop plants so as to make the plants more nutritious and palatable for animals.

DESCRIPTION

I have now found that certain related compounds, many of which are new, surprisingly have good herbicidal activity which may make them of use as herbicides, and particularly as selective herbicides, in agriculture.

Accordingly, in one aspect, this invention provides a herbicidal composition which comprises one or more compounds of the formula:

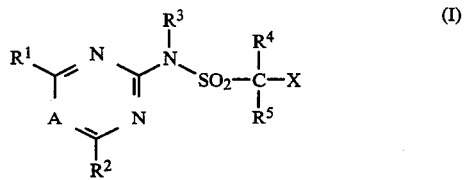

or salts thereof, where:

A is —CH= or —N=;
$R^1$ is alkyl, alkoxy, halo or —NR$^7$R$^8$;
$R^2$ is alkyl or alkoxy;
$R^3$ is hydrogen, alkenyl or alkynyl, or substituted or unsubstituted alkyl, alkanoyl or alkoxycarbonyl;
$R^4$ is hydrogen or substituted or unsubstituted alkyl;
$R^5$ is halo or substituted or unsubstituted alkyl or aryl; and
X is —CO$_2$R$^6$, —CONR$^7$R$^8$ or —CN;
in which $R^6$, $R^7$ and $R^8$ which may be the same or different, each represent hydrogen, substituted or unsubstituted alkyl, or one of $R^7$ and $R^8$ represents substituted amino;
in association with a suitable carrier and/or surface active agent.

In another aspect, the invention provides per se the compounds of formula I in which $R^5$ represents isopropyl, and/or X represents methoxycarbonyl, and salts thereof.

In a further aspect, the invention provides a method of combating weeds at a locus infested or liable to be infested therewith which comprises applying to said locus an effective amount of one or more compounds of formula I or salts thereof.

Any alkyl group present in the compound of formula I is preferably of 1 to 6 carbon atoms, especially of 1 to 4 carbon atoms. Specific preferred unsubstituted alkyl or alkyl-containing groups include methyl, ethyl, n-propyl, isopropyl, n-butyl, t-butyl, methoxy, ethoxy and n-propoxy. When the alkyl group may be substituted, it is preferably substituted for example by one or more halogen atoms, e.g. fluorine, chlorine or bromine, or by alkoxy groups of 1 to 4 carbon atoms, e.g. methoxy or ethoxy. Specific preferred substituted alkyl-containing groups include chloromethyl, bromomethyl, dichloromethyl, trifluoromethyl, difluoromethoxy, methoxyethyl and ethoxyethyl.

Any alkenyl or alkynyl group in the compound of formula I is preferably of 2 to 6 carbon atoms, for example allyl or propargyl.

Any halogen atom present in the compound of formula I is preferably fluorine, chlorine or bromine.

When $R^5$ represents an aryl group, it is preferably a substituted or unsubstituted phenyl group. When substituted, it is preferably substituted by one or more halogen atoms, e.g. chlorine, fluorine or bromine atoms, nitro groups, substituted or unsubstituted amino groups (e.g. alkylamino, dialkylamino or acylamino groups, especially where the alkyl moieties have from 1 to 4 carbon atoms), cyano groups, or alkyl or alkoxy groups of 1 to 4 carbon atoms, e.g. methyl, ethyl, methoxy or ethoxy.

A preferably represents —CH=.

$R^1$ is preferably chloro, methoxy, ethoxy or dimethylamino.

$R^2$ is preferably methoxy or ethoxy.

In a particularly preferred group of compounds of formula I, $R^1$ and $R^2$ are both methoxy.

$R^3$ is preferably hydrogen, methyl, ethyl, allyl, propargyl, acetyl or methoxycarbonyl, particularly hydrogen.

$R^4$ is preferably hydrogen.

$R^5$ is preferably isopropyl.

X is preferably carboxy, methoxycarbonyl, ethoxycarbonyl, carbamoyl or methylcarbamoyl, particularly methoxycarbonyl.

The salts of the compounds of formula I are preferably those formed with alkali-metals, e.g. lithium, sodium or potassium, or organic bases, e.g. amines such as cyclohexylamine or piperidine.

Specific preferred compounds according to the invention are those of the Examples provided hereinafter. Particular mention may, however, be made of methyl 2-(4,6-dimethoxypyrimidin-2-ylsulfamoyl)-3-methylbutanoate, the salts thereof, and the analogues thereof wherein $R^3$ is other than hydrogen, which break down in use to the compound where $R^3$ is hydrogen.

The compounds of the invention where $R^3$ represents hydrogen and X is a group —CO$_2$R$^6$ can be prepared by a process in which a compound of the formula:

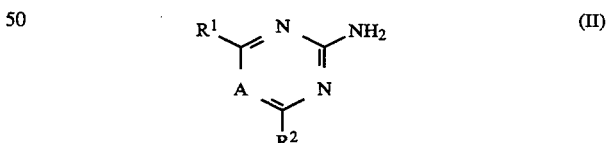

where A, $R^1$ and $R^2$ are as defined hereinbefore, is reacted in the presence of a base with a compound of the formula:

where $R^4$ and $R^5$ are as defined hereinbefore, and X is a group —CO$_2$R$^6$ as defined hereinbefore, to give the desired compound.

The base employed is preferably an organic amine, especially pyridine.

The reaction is desirably effected in an appropriate solvent medium, for example dichloromethane, and with cooling, e.g. to a temperature of from 0° to 20° C.

The compounds of formula II are themselves known compounds, or can be made by processes analogous to those used to prepare related known compounds.

The compounds of formula III may be prepared by a two-stage process in which a compound of the formula:

where $R^4$ and $R^5$ are as defined hereinbefore, and X represents a group $-CO_2R^6$ is reacted with thiolacetic acid in the presence of a base to give the corresponding compound of the formula:

which is then chlorinated to give the corresponding compound of formula III.

In the first stage, the reaction is preferably effected in a suitable solvent medium, for example in dimethylformamide, with cooling to a temperature of from 0° to 20° C. The base employed may conveniently be potassium t-butoxide.

In the second stage, the chlorination is desirably effected by passing chlorine gas through a suspension of the starting material in aqueous hydrochloric acid, again with cooling to maintain the temperature between 0° and 20° C.

The compounds of formula I where $R^3$ is alkyl, alkenyl, alkynyl or alkanoyl may be made from the corresponding compounds where $R^3$ is hydrogen by alkylation, alkenylation, alkynylation or acylation reactions known per se using one equivalent of base.

The compounds of formula I where $R^3$ is alkoxycarbonyl may be prepared from the corresponding compounds in which $R^3$ is hydrogen by reaction thereof with a suitable alkyl chloroformate in the presence of a base.

The compounds of formula I in which $R^4$ is alkyl may be prepared from the corresponding compounds where $R^4$ is hydrogen by alkylation techniques known per se using two equivalents of base.

The compounds of formula I where X is a group $CONR^7R^8$ may be prepared from the corresponding compounds where X is $-COOR^6$ by amination reactions known per se.

The compounds of formula I where X is $-CN$ may be prepared from the corresponding compounds where X is $-CONH_2$ by dehydration techniques known per se.

The salts of the compounds of formula I may be prepared by reaction of the corresponding unsalified compound of formula I with an appropriate salt-forming base by methods known per se.

The compounds of formula I may of course be interconverted by methods known per se into further compounds of formula I. For example, the compounds in which X represents carboxy may be prepared by hydrolysis of the corresponding compounds where X represents an ester grouping.

The compounds of formula I and the salts thereof are herbicidally-active against a wide range of weeds, especially broad leaved weeds, including cleavers (Galium spp), but are comparatively safe to certain crop species. They may thus be of use as herbicides, and especially as selective herbicides, particularly in cereals, e.g. maize, wheat, barley, or rice, or in cotton.

The compositions of the invention usually contain from 0.01 to 99% by weight of the present compounds, and are normally produced initially as concentrates containing from 0.5 to 99%, preferably from 0.5 to 85%, and especially from 10 to 50% by weight thereof. Such concentrates are diluted if necessary before application to the locus to be treated such that the active ingredient comprises from 0.01 to 5% by weight of the formulation applied.

The carrier may be water, in which case an organic solvent may also be present, though this is not usually employed. A flowable suspension concentrate may be formed by grinding the compound with water, a wetting agent and a suspending agent, e.g. xanthan gum.

The carrier may alternatively be a water immiscible organic solvent, e.g. a hydrocarbon which boils within the range 130°-270° C., e.g. xylene, in which the compound is dissolved or suspended. An emulsifiable concentrate containing a water immiscible solvent may be formed with a surface active agent so that the concentrate acts as a self-emulsifiable oil on admixture with water.

The carrier may alternatively be a water-miscible organic solvent e.g. 2-methoxyethanol, methanol, propylene glycol, diethylene glycol, diethylene glycol monoethyl ether, methylformamide or dimethylformamide.

The carrier may alternatively be a solid, which may be finely divided or granular. Examples of suitable solids are limestone, clays, sand, mica, chalk, attapulgite, diatomite, perlite, sepiolite, silicas, silicates, lignosulfonates and solid fertilizers. The carrier can be natural or synthetic or can be modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant, e.g. a polyhalogenated alkane such as dichlorofluoromethane, and suitably also with a solvent.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with a fatty alcohol ethoxylate, or salts of such esters, fatty alcohol sulfates such as sodium dodecyl sulfate, ethoxylated fatty alcohol sulfates, ethoxylated alkylphenol sulfates, lignin sulfates, petroleum sulfonates, alkylaryl sulfonates such as alkyl-benzene sulfonates or lower alkylnaphthalene sulfonates, salts of sulfonated naphthaleneformaldehyde condensates, salts of sulfonated phenolformaldehyde condensates, or more complex sulfonates such as the amide sulfonates, e.g. the sulfonated condensation product of oleic acid and N-methyl taurine or the dialkyl sulfosuccinates e.g. the sodium sulfonate of dioctyl succinate.

The surface active agents may also comprise non-ionic agents, for example condensation products or fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quaternary ammonium compounds such as cetyl trimethylammonium bromide, or ethoxylated tertiary fatty amines.

Preferred surface active agents include ethoxylated fatty alcohol sulfates, lignin sulfonates, alkyl-aryl sulfonates, salts of sulfonated naphthaleneformaldehyde condensates, salts of sulfonated phenolformaldehyde condensates, sodium oleoyl N-methyltauride, dialkyl sulfosuccinates, alkyl phenol ethoxylates, and fatty alkyl ethoxylates.

The present active compounds may be admixed with another pesticide, e.g. a herbicide, fungicide or insecticide, or a plant growth regulator, particularly another herbicide. Suitable further herbicides include trietazine, linuron, MCPA, dichlorprop, isoxaben, diflufenican, metolachlor, fluometuron, oxyfluorfen, fomesafen, bentazone, prometryne, norflurazon, chlomazone, EPTC, imazaquin, and especially isoproturon, methabenzthiazuron, trifluralin, ioxynil, bromoxynil, benazolin, mecoprop, fluroxypyr, alachlor, acifluorfen, lactofen, metribuzin, pendimethalin, ethofumesate, benfuresate, phenmedipham, benzophenap, butachlor, chlomethoxyfen, dimepiperate, mefenacet, molinate, naproanilide, oxadiazon, piperophos, prometryne, pyrazoxyfen, pyrazosulfuron-ethyl, bensulfuron, simetryne, pyrazolate, pretilachlor, thiobencarb and pyributicarb.

The present compounds may be applied to plants, the soil, land or aquatic areas, and particularly to a locus at which a crop is growing. The compounds are active both pre- and post-emergence, and may be employed at rates of from 20 g to 2 kg/ha.

The invention is illustrated by the following Examples, in which Me=methyl, Et=ethyl, Pr=propyl, Bu=butyl, Ph=phenyl, i=iso, and s=secondary.

Example 1

Methyl 2-(4,6-dimethoxypyrimidin-2-ylsulfamoyl)-3-methylbutanoate a) Methyl 2-acetylthio-3-methylbutanoate Potassium tert-butoxide (20.4 g) was added portionwise with stirring and cooling to thioacetic acid (13.85 g) in dry dimethylformamide (150 ml). Stirring was continued for five minutes, then methyl 2-bromo-3-methylbutanoate (32.3 g) was added with ice-cooling (about 10° C. internal temperature). After stirring at room temperature overnight, the reaction mixture was diluted with ether (about 1 liter), washed with water (3 times), dried over magnesium sulfate and run down under vacuum. The title product was obtained as an orange oil, 29.2 g (93%).

b) Methyl 2-chlorosulfonyl-3-methylbutanoate

Chlorine was bubbled, with vigorous stirring into a suspension of the product of stage (a) (29.2 g) in a mixture of water (300 ml) and concentrated hydrochloric acid (30 ml) at about 10° C. (ice-cooling required) over 2 hours. The organic phase was then extracted into ether, the ether solution washed with water (3 times), dried over magnesium sulfate and run down under vacuum yielding 23.2 g crude title product. Distillation gave 12.4 g (bp 65°-6° C. at 0.3 mm Hg) of pure product (35%).

c) Methyl 2-(4,6-dimethoxypyrimidin-2-ylsulfamoyl)-3-methylbutanoate

The product of stage (b) (5.47 g) in dichloromethane (10 ml) was added dropwise with stirring and cooling (temperature 5°-10° C.) to 2-amino-4,6-dimethoxypyrimidine (4.0 g) and dry pyridine (2.21 g) in dichloromethane (30 ml). The mixture was stirred for 4 hours and allowed to stand overnight at room temperature. The dichloromethane solution was washed with water, dilute hydrochloric acid, and water again (twice), dried over magnesium sulfate and run down under vacuum. The residue was triturated with petroleum ether (bp 40°-60° C.) to give the title product as a white solid, mp 94°-95° C., in a yield of 6.6 g (78%).

Examples 2-11

The following compounds of formula I where A is —CH=, and $R^3$ and $R^4$ are hydrogen were prepared by processes analogous to those described in Example 1:

| Ex | $R^1$ | $R^2$ | $R^3$ | X | M Pt °C. |
| --- | --- | --- | --- | --- | --- |
| 2 | OMe | OMe | i-Pr | COOEt | 79-82 |
| 3 | OEt | OEt | i-Pr | COOMe | 73-76 |
| 4 | Cl | OMe | i-Pr | COOMe | 103-106 |
| 5 | Cl | OEt | i-Pr | COOMe | 72-75 |
| 6 | OMe | OMe | s-Bu | COOMe | oil |
| 7 | OMe | OMe | i-Bu | COOMe | oil |
| 8 | OMe | OMe | n-Pr | COOMe | 83.5-85 |
| 9 | OMe | OMe | Me | COOMe | 94-96 |
| 10 | OMe | OMe | Et | COOMe | 67-68 |
| 11 | OMe | OMe | Ph | COOMe | 128-131 |

Example 12

Methyl 2-[N-(4,6-dimethoxypyrimidin-2-yl)-N-methylsulfamoyl]-3-methylbutanoate

Potassium tert-butoxide (1.4 g) was added with stirring and cooling to the product of Example 1 (4.0 g) in dimethylformamide (25 ml). Iodomethane (1.78 g) was added portionwise, stirring was continued for 2 hours and the reaction mixture was allowed to stand at room temperature for 8 days. Addition to water and isolation through ethyl acetate gave the crude title product as a yellow oil. Purification by flash chromatography on silica gel in 10% ethyl acetate/dichloromethane gave 2.3 g (55%) pure product as a pale yellow oil.

Examples 13-15

The following compounds of formula I where A is —CH=, $R^4$ is hydrogen and $R^5$ is isopropyl were prepared by processes analogous to those described in Example 6:

| Ex | $R^1$ | $R^2$ | $R^3$ | X | M Pt °C. |
| --- | --- | --- | --- | --- | --- |
| 13 | OMe | OMe | OMe | COOEt | oil |

-continued

| Ex | R¹ | R² | R³ | X | M Pt °C. |
|----|-----|-----|------------|-------|----------|
| 14 | OMe | OMe | CH₂CH=CH₂ | COOMe | oil |
| 15 | OMe | OMe | propargyl | COOMe | oil |

Example 16

2-(4,6-Dimethoxypyrimidin-2-ylsulfamoyl)-3-methylbutanoic acid

The product of Example 2 (1.0 g) was treated with sodium hydroxide (0.46 g) in water (10 ml), and the mixture was allowed to stand at room temperature for 3 weeks. Acidification (hydrochloric acid) followed by filtration gave, after washing with water and ether and drying, the title compound as a white solid (0.7 g), mp 187°–188° C. decomp.

Examples 17–18

The following compounds of formula I where A is —CH=, R⁴ is hydrogen and R⁵ is isopropyl were prepared by processes analogous to those described in Example 16:

| Ex | R¹ | R² | R³ | X | M Pt °C. |
|----|-----|-----|-----------|------|----------|
| 17 | OMe | OMe | Me | COOH | 110–112 |
| 18 | OMe | OMe | propargyl | COOH | 119–120 |

Example 19

Methyl 2-[N-(4,6-dimethoxypyrimidin-2-yl)-N-acetylsulfamoyl]-3-methylbutanoate

Acetyl chloride (0.35 g) was added to a stirred, cooled mixture of the product of Example 1 (1.5 g) and pyridine (0.39 g) in dichloromethane (20 ml). Stirring was continued for 2 hours and the mixture was allowed to stand overnight. The organic solution was washed with water (twice), dried over magnesium sulfate and run down under vacuum. The residue was triturated with ether to yield a white solid, 0.38 g (23%), mp 100°–101.5° C.

Example 20

2-(4,6-dimethoxypyrimidin-2-ylsulfamoyl)-3-methylbutanamide

A solution of the product of Example 1 (3.0 g) and formamide (1.22 g) in dimethylformamide (10 ml) was heated to 80° C. Sodium methoxide (3.3 ml of a 25% w/v methanol solution) was slowly introduced with stirring. The reaction mixture was maintained at about 100° C. for 4 hours prior to addition to water (150 ml) and acidification (hydrochloric acid). The product was extracted into ethyl acetate, the ethyl acetate solution being washed with water (twice), dried over magnesium sulfate and run down under vacuum. The residual oil was triturated with a mixture of diethyl and diisopropyl ethers to yield a white solid. The solid was washed thoroughly with the ether mixture and dried. The yield was 1.1 g (39%), mp 147°–50° C.

Example 21

The following compound of formula I where A is —CH=, R³ and R⁴ are hydrogen, and R⁵ is isopropyl was prepared by a process analogous to that described in Example 20:

| Ex | R¹ | R² | X | M Pt °C. |
|----|-----|-----|--------|----------|
| 21 | OMe | OMe | CONHMe | 150–152 |

Example 22

Methyl 2-(4,6-dimethoxypyrimidin-2-ylsulfamoyl)-3methylbutanoate cyclohexylamine salt A solution of the product of Example 1 (1.0 g) in ether (35 ml) was treated dropwise, with stirring and cooling, with cyclohexylamine (0.3 g) in ether (7 ml). The mixture was stirred for one hour and allowed to stand overnight at room temperature. The precipitated salt was filtered off, washed with ether and dried, yielding 1.15 g (88%), mp 158°–160° C.

Example 23

Methyl 2-(4,6-dimethoxypyrimidin-2-ylsulfamoyl)-3methylbutanoate piperidinium salt The above compound, mp 143°–144° C., was prepared by a method analogous to that of Example 22.

Example 24

Methyl 2-[4-dimethylamino-6-methoxy-2-(1,3,5-triazinyl)sulfamoyl]-3-methylbutanoate Methyl 2-chlorosulfonyl-3-methylbutanoate (3.2 g) was added dropwise to a stirred, ice-cooled solution of 2-amino-4-dimethylamino-6-methoxy-1,3,5-triazine (2.5 g) in pyridine (40 ml). After stirring for 2 hours and standing at room temperature for 3 days, the reaction mixture was added to water and acidified by the addition of hydrochloric acid. Filtration, followed by washing with water, acetone and ether gave the desired product (2.7 g), mp 185°–189° C.

Example 25

Methyl 2-(4,6-dimethoxy-1,3,5-triazin-2-ylsulfamoyl]-3-methylbutanoate

The above compound was prepared by a process analogous to that of Example 24, mp 105°–108.5° C.

Example 26

Methyl 2-(4,6-dimethoxypyrimidin-2-ylsulfamoyl)-2,3-dimethylbutanoate

Potassium t-butoxide (5.3 g) was added with stirring and cooling to the product of Example 1 (7.5 g) in dry tetrahydrofuran (120 ml). The mixture was stirred for 4½ hours at room temperature, and was then cooled to 5° C., when iodomethane (3.2 g) in dry tetrahydrofuran (10 ml) was added dropwise. Stirring was continued at room temperature for 24 hours, and the intermittently for 7 days. The solvent was run off under vacuum, and the residue was stirred with ice, water and ether while being acidified to pH=1 with hydrochloric acid. The ether solution was separated, the aqueous layer being extracted twice more with ether, and the combined ether extracts were washed with water (twice), dried over magnesium sulfate, and run down under vacuum to give the desired product (7.1 g) in am impure form. Purification by flash chromatography on silica gel, eluting with dichloromethane and ethyl acetate (9:1), followed by preparative HPLC gave 0.4 g of the pure desired product, mp 124°-127° C.

Example 27

2-(4,6-Dimethoxypyrimidin-2-ylsulfamoyl)-3-methyl-butanonitrile

Trifluoroacetic anhydride (0.73 g) was added to a stirred, ice-cooled solution of the product of Example 20 in dioxan (10 ml) containing pyridine (0.5 g). After stirring for 1½ hours at room temperature, the mixture was added to water (100 ml) and acidified with hydrochloric acid. The liberated product was extracted into ether, and the ether solution was washed with water (twice), dried over magnesium sulfate and run down. The residual oil was flash chromatographed on silica gel, eluting with 30% ethyl acetate in dichloromethane, to give, after trituration with petroleum ether (bp 40°-60° C.), 0.3 g of the desired product, mp 91°-93° C., as a white solid.

Example 28

Methyl 2-([N-(4,6-dimethoxypyrimidin-2-yl)-N-(methoxycarbonyl)sulfamoyl]-3-methylbutanoate

Methyl chloroformate (0.6 g) in dichloromethane (5ml) was added to stirred, ice-cooled product of Example 1 (2 g) and triethylamine (0.67 g) in dichloromethane (40 ml). After stirring for 2 hours, the mixture was allowed to stand at room temperature for 4 weeks. Dilution with ether, washing with dilute hydrochloric acid and water, drying over magnesium sulfate and running down gave a pink oil. Flash chromatography on silica gel, eluting with 10% ethyl acetate in dichloromethane gave 1.1 g of the desired product as a clear oil.

Herbicidal Example A (Pre-Emergence)

Seeds of the test species listed below were each sown in 8.5 cm square pots filled to within 2 cm of the top with sterile loam, and were covered with a 2-5 mm layer of loam. The pots were watered, and then treated by application to the soil surface in a spray cabinet with the compounds of the Examples listed below formulated as a solution/suspension in 3:1 by volume of acetone and the wetting agent polyoxyethylene (20 mols) monolaurate solution (10 g per liter). The concentration of each test compound and volume of application were calculated to give the desired rate of application of the compound in 200 liters per hectare.

After 3 to 4 weeks growth in a glasshouse (minimum temperature 16° C. for temperate species, 21° C. for non-temperate species, 16 hours per day photoperiod) the plants were visually assessed for any herbicidal response. All differences from an untreated control were scored accordingly to an index where 0=no effect, 1=1-24% effect, 2=25-69% effect, 3=70-89% effect and 4==90-100% effect. In the table below, the following letters are used to denote the plant species:

a-*Triticum aestivum* (wheat)
b-*Hordeumvulgare* (barley)
c-*Beta vulgaris* (sugar beet)
d-*Brassica napus* (rape)
e-*Alopecurus myosuroides* (blackgrass)
f-*Avena fatua* (wild oat)
g-*Elymus repens* (couch)
h-*Bromus sterilis* (barren brome)
i-*Viola arvensis* (field pansy)
j-*Stellaria media* (chickweed)
k-*Galium aparine* (cleavers)
l-*Matricaria inodora* (scentless mayweed)
m-*Polygonum lapathifolium* (Pale persicaria)
n-*Veronica persica* (Buxbaum's speedwell).

The results obtained were as follows:

| Ex | Kg/ha | a | b | c | d | e | f | g | h | i | j | k | l | m | n |
|---|---|---|---|---|---|---|---|---|---|---|---|---|---|---|---|
| 1 | 1.0 | 2 | 1 | 4 | 4 | 2 | 2 | 2 | 1 | 4 | 4 | 3 | 4 | 4 | 4 |
| 2 | 2.0 | 1 | 1 | 3 | 4 | 2 | 1 | 3 | 2 | 4 | 3 | 2 | — | 3 | — |
| 3 | 2.0 | 0 | 1 | 2 | 2 | 0 | 1 | 1 | 2 | 0 | 3 | 0 | 3 | 2 | 3 |
| 4 | 2.0 | 1 | 2 | 2 | 3 | 2 | 0 | 1 | 1 | 2 | 2 | 4 | 3 | 3 | |
| 6 | 0.25 | 1 | 1 | 2 | 2 | 0 | 1 | 0 | 0 | 2 | 2 | 0 | 2 | 2 | 3 |
| 12 | 2.0 | 1 | 1 | 1 | 2 | 0 | 0 | 0 | 0 | 4 | 0 | 4 | 2 | 1 | 0 |
| 15 | 0.5 | 0 | 0 | 2 | 3 | 2 | 1 | 2 | 1 | 4 | 2 | 2 | 4 | 2 | 3 |
| 16 | 2.0 | 0 | 1 | 0 | 0 | 2 | 4 | 2 | 4 | 2 | 2 | 0 | 3 | — | |
| 19 | 1.0 | 2 | 2 | 4 | 4 | 2 | 1 | 2 | 2 | 4 | 3 | 3 | 4 | 4 | 4 |
| 20 | 0.5 | 0 | 0 | 2 | 4 | 1 | 0 | 0 | 0 | 2 | 3 | 2 | 3 | 3 | 2 |
| 21 | 0.5 | 0 | 0 | 2 | 3 | 2 | 0 | 2 | 0 | 2 | 2 | 2 | 2 | 3 | 2 |
| 22 | 1.0 | 1 | 2 | 4 | 4 | 3 | 2 | 2 | 1 | 4 | 4 | 4 | 4 | 4 | 4 |
| 23 | 1.0 | 1 | 1 | 4 | 4 | 2 | 2 | 2 | 0 | 4 | 4 | 4 | 4 | 4 | 4 |

Herbicidal Example B (Post-Emergence)

The plant species listed below were grown in 8.5 cm square pots containing sterile loam in a glasshouse (minimum temperature 16° C. for temperate species, 21° C. for non-temperate species, 16 hours per day photoperiod), and were treated in a spray cabinet at the 2-3 leaf stage with the compounds of the Examples listed below formulated as a solution/suspension in 1:1 by volume of acetone and the wetting agent polyoxyethylene (20 mols) monolaurate solution (2 g per liter). The concentration of each test compound and volume of application were calculated to give the desired rate of application of the compound in 200 liters per hectare. After 3-4 weeks, the plants were visually assessed for any herbicidal response. All differences from an untreated control were scored according to an index where 0=no effect, 1=1-24% effect, 2=25-69% effect, 3=70-89% effect and 4=90-100% effect.

In the results below, the letters used denote the same plant species as in Herbicidal Example A:

| Ex | Kg/ha | a | b | c | d | e | f | g | h | i | j | k | l | m | n |
|---|---|---|---|---|---|---|---|---|---|---|---|---|---|---|---|
| 1 | 1.0 | 1 | 1 | 4 | 4 | 3 | 2 | 2 | 1 | 4 | 4 | 4 | 4 | 3 | 4 |

| Ex | Kg/ha | a | b | c | d | e | f | g | h | i | j | k | l | m | n |
|---|---|---|---|---|---|---|---|---|---|---|---|---|---|---|---|
| 2 | 2.0 | 0 | 2 | 3 | 4 | 2 | 1 | 1 | 1 | 4 | 2 | 3 | 2 | 3 | — |
| 4 | 2.0 | 0 | 1 | 2 | 4 | 1 | 0 | 1 | 0 | 2 | 1 | 2 | 3 | 1 | 0 |
| 10 | 1.0 | 1 | 2 | 4 | 4 | 1 | 0 | 1 | 1 | 3 | 2 | 4 | 3 | 3 | 2 |
| 12 | 2.0 | 0 | 0 | 3 | 2 | 1 | 0 | 0 | 1 | 3 | 0 | 3 | 0 | 1 | 0 |
| 14 | 1.0 | 0 | 1 | 2 | 3 | 2 | 1 | 0 | 2 | 2 | 0 | 3 | 0 | 2 | 0 |
| 15 | 1.0 | 1 | 2 | 2 | 4 | 2 | 2 | 0 | 1 | 4 | 2 | 4 | 1 | 3 | 2 |
| 19 | 0.5 | 0 | 2 | 4 | 4 | 2 | 0 | 0 | 0 | 4 | 3 | 4 | 3 | 4 | 3 |
| 22 | 1.0 | 1 | 2 | 4 | 4 | 3 | 0 | 2 | 0 | 4 | 4 | 4 | 4 | 4 | 4 |
| 23 | 1.0 | 1 | 2 | 4 | 4 | 2 | 1 | 2 | 1 | 3 | 3 | 4 | 4 | 4 | 3 |
| 24 | 0.5 | 1 | 2 | 3 | 4 | 2 | 0 | 2 | 0 | 2 | 3 | 2 | 2 | 3 | 2 |
| 25 | 0.5 | 1 | 0 | 4 | 4 | 2 | 0 | 1 | 0 | 2 | 2 | 3 | 3 | 4 | 0 |

I claim:

1. A herbicidal composition comprising at least one compound of the formula:

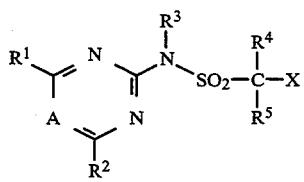

or salts thereof, where:

A is —CH=;

$R^1$ is $C_{1-6}$ alkyl, $C_{1-6}$ alkoxy, halo or —$NR^7R^8$;

$R^2$ is $C_{1-6}$ alkyl or $C_{1-6}$ alkoxy;

$R^3$ is hydrogen, $C_{2-6}$ alkenyl or $C_{2-6}$ alkynyl, or alkyl, alkanoyl or alkoxycarbonyl in which the alkyl moiety is of 1 to 6 carbon atoms, and is either unsubstituted or substituted by one or more halogen atoms or alkoxy groups of 1 to 4 carbon atoms;

$R^4$ is hydrogen or $C_{1-6}$ alkyl which is either unsubstituted or substituted by one or more halogen atoms or alkoxy groups of 1 to 4 carbon atoms;

$R^5$ is halo or $C_{1-6}$ alkyl which is either unsubstituted or substituted by one or more halogen atoms or alkoxy groups of 1 to 4 carbon atoms or phenyl which is either unsubstituted or substituted by one or more halogen atoms, nitro groups, amino groups, alkylamino, dialkylamino or acylamino groups (in which the alkyl moieties are each of 1 to 4 carbon atoms), cyano groups, or alkyl or alkoxy groups of 1 to 4 carbon atoms; and X is —$CO_2R^6$, $CONR^7R^8$ or —CN;

in which $R^6$, $R^7$ and $R^8$, which may be the same or different, each represent hydrogen, $C_{1-6}$ alkyl which is either unsubstituted or substituted by one or more halogen atoms or alkoxy groups of 1 to 4 carbon atoms, or one of $R^7$ and $R^8$ represents alkylamino, dialkylamino or acylamino groups (in which the alkyl moieties are each of 1 to 4 carbon atoms);

in association with a suitable carrier or surface active agent or both.

2. A herbicidal composition according to claim 1 where $R^1$ in the compound of formula I is chloro, methoxy, ethoxy or dimethylamino, and $R^2$ is methoxy or ethoxy.

3. A herbicidal composition according to claim 1 where $R^3$ in the compound of formula I is hydrogen; alkyl, alkanoyl or alkoxycarbonyl in which the alkyl group is of 1 to 6 carbon atoms; or alkenyl or alkynyl of 2 to 6 carbon atoms.

4. A herbicidal composition according to claim 1 where $R^5$ in the compound of formula I is alkyl of 1 to 6 carbon atoms.

5. A herbicidal composition according to claim 4 in which $R^5$ in the compound of formula I is isopropyl.

6. A herbicidal composition according to claim 1 where X in the compound of formula I is alkoxycarbonyl in which the alkyl group is of 1 to 6 carbon atoms.

7. A herbicidal composition according to claim 6 where X in the compound of formula I is methoxycarbonyl.

8. A herbicidal composition according to claim 7 where $R^1$ and $R^2$ are methoxy, $R^4$ is hydrogen, and $R^5$ is isopropyl.

9. A herbicidal compound of the formula:

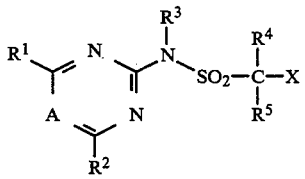

or salts thereof, where:

A is —CH=;

$R^1$ is $C_{1-6}$ alkyl, $C_{1-6}$ alkoxy, halo or —$NR^7R^8$;

$R^2$ is $C_{1-6}$ alkyl or $C_{1-6}$ alkoxy;

$R^3$ is hydrogen, $C_{2-6}$ alkenyl or $C_{2-6}$ alkynyl, or alkyl, alkanoyl or alkoxycarbonyl in which the alkyl moiety is of 1 to 6 carbon atoms, and is either unsubstituted or substituted by one or more halogen atoms or alkoxy groups of 1 to 4 carbon atoms;

$R^4$ is hydrogen or $C_{1-6}$ alkyl which is either unsubstituted or substituted by one or more halogen atoms or alkoxy groups of 1 to 4 carbon atoms;

$R^5$ is halo or $C_{1-6}$ alkyl which is either unsubstituted or substituted by one or more halogen atoms or alkoxy groups of 1 to 4 carbon atoms or phenyl which is either unsubstituted or substituted by one or more halogen atoms, nitro groups, amino groups, alkylamino, dialkylamino or acylamino groups (in which the alkyl moieties are each of 1 to 4 carbon atoms), cyano groups, or alkyl or alkoxy groups of 1 to 4 carbon atoms; and;

X is —$CO_2R^6$, —$CONR^7R^8$ or —CN;

in which $R^6$, $R^7$ and $R^8$, which may be the same or different, each represent hydrogen, $C_{1-6}$ alkyl which is either unsubstituted or substituted by one or more halogen atoms or alkoxy groups of 1 to 4 carbon atoms, or one of $R^7$ and $R^8$ represents alkylamino, dialkylamino or acylamino groups (in which the alkyl moieties are each of 1 to 4 carbon atoms);

with the proviso that one or both of the following is true: (a) $R^5$ represents isopropyl and (b) X represents methoxycarbonyl.

10. A compound according to claim 9 where $R^1$ is chloro, methoxy, ethoxy or dimethylamino, and $R^2$ is methoxy or ethoxy.

11. A compound according to claim 10 where $R^1$ and $R^2$ are methoxy, $R^3$ is hydrogen, methyl, ethyl, allyl, propargyl, acetal or methoxycarbonyl, $R^4$ is hydrogen, $R^5$ is isopropyl and X is carboxy, methoxycarbonyl, ethoxycarbonyl, carbamoyl or methylcarbamoyl.

12. A compound according to claim 10 in which $R^1$ is methoxy or chloro, $R^2$ is methoxy, $R^3$ is hydrogen, methyl or propargyl, $R^4$ is hydrogen or methyl, $R^5$ is isopropyl and X is carboxy, methoxycarbonyl or ethoxycarbonyl.

13. A compound according to claim 9 in which $R^1$ and $R^2$ are methoxy, $R^4$ is hydrogen, $R^5$ is isopropyl and X is methoxycarbonyl.

14. A compound according to claim 13, in which $R^3$ is hydrogen.

15. A method of combatting weeds and locus infested or liable to be infested therewith which comprises apply to said locus an effective amount of at least one compound according to claim 9 or salt thereof.

16. A method of combatting weeds and locus infested or liable to be infested therewith which comprises apply to said locus an effective amount of at least one compound according to claim 10 or salt thereof.

17. A method of combatting weeds and locus infested or liable to be infested therewith which comprises apply to said locus an effective amount of at least one compound according to claim 11 or salt thereof.

18. A method of combatting weeds and locus infested or liable to be infested therewith which comprises apply to said locus an effective amount of at least one compound according to claim 12 or salt thereof.

19. A method of combatting weeds and locus infested or liable to be infested therewith which comprises apply to said locus an effective amount of at least one compound according to claim 13 or salt thereof.

20. A method of combatting weeds and locus infested or liable to be infested therewith which comprises apply to said locus an effective amount of at least one compound according to claim 14 or salt thereof.

* * * * *